US00PP12604P2

(12) United States Plant Patent
Gross

(10) Patent No.: US PP12,604 P2
(45) Date of Patent: May 7, 2002

(54) POINSETTIA PLANT NAMED 'AMAZONE'

(75) Inventor: Eric Gross, Voulgezac (FR)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/563,938

(22) Filed: May 4, 2000

(51) Int. Cl.[7] ..... A01H 5/00

(52) U.S. Cl. ..... Plt./306

(58) Field of Search ..... Plt./306

(56) References Cited

U.S. PATENT DOCUMENTS

PP7,231 P * 5/1990 Fruehwirth ..... 799/86

* cited by examiner

*Primary Examiner*—Bruce R. Campell
*Assistant Examiner*—Anne Marie Grunberg
(74) *Attorney, Agent, or Firm*—C. A. Whealy

(57) ABSTRACT

A new and distinct culitvar of Poinsettia plant named 'Amazone', characterized by its attractive pink and darker pink-speckled bracts; dark green leaves; compact, uniform, upright and spreading plant habit; very freely branching habit; early flowering; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Amazone'.

The new Poinsettia a product of a planned breeding program conducted by the Inventor in Blanzac, France. The objective of the breeding program is to create new Poinsettia cultivars having flower bracts with desirable colors, uniform plant habit and excellent post-production longevity.

The new Poinsettia originated from a cross made by the Inventor of two unidentified proprietary Poinsettia selections. The cultivar Amazone was discovered and selected by the Inventor as a flowering plant within the progeny of the stated cross in a controlled environment in Blanzac, France, in March, 1997. The selection of this plant was based on its attractive flower bract colors and good form and substance.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Amazone'. These characteristics in combination distinguish 'Amazone' as a new and distinct cultivar:

1. Pink and darker pink-speckled bracts.
2. Dark green leaves.
3. Compact, uniform, upright and spreading plant habit.
4. Very freely branching habit.
5. Early flowering.
6. Excellent post-production longevity.

Plants of the new Poinsettia can be compared to plants of the Poinsettia cultivar 221 , disclosed in U.S. Plant Pat. No. 7,231. In side-by-side comparisons conducted in Encinitas, Calif., plants of the new Poinsettia differed from plants of the cultivar 221 in the following characteristics:

1 1. Plants of the new Poinsettia are more compact and more uniform in plant habit than plants of the cultivar 221.

1 2. Plants of the new Poinsettia are much more freely branching and much denser and fuller than plants of the cultivar 221.

1 3. Plants of the new Poinsettia have stronger stems than plants of the cultivar 221.

1 4. Leaves of the new Poinsettia are slightly broader and are held more upright than leaves of the cultivar 221.

1 5. Plants of the new Poinsettia have rounder and more uniformly-shaped inflorescences than plants of the cultivar 221.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the actual colors of the new Poinsettia.

The photograph at the top of the first sheet comprises a side perspective view of a typical plant of 'Amazone'.

The photograph at the bottom of the first sheet comprises a top perspective view of a typical plant of 'Amazone'.

The photograph on the second sheet is a close-up view of typical bracts and leaves of 'Amazone' (left) and '221 '(right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 21 to 27° C., night temperatures about 18 to 20° C., and light levels about 4,000 foot-candles. Plants were grown in 16.5-cm pots, pinched one time, and flowered under naturally lengthening nights during the fall.

In the following description, color references are made to The Royal Horticultural Society Colour Chart except where general terms of ordinary dictionary significance are used.

Botanical classification: *Euphorbia pulcherrima* Willd. cultivar Amazone.

Parentage:

*Female parent.*—Unidentified proprietary Poinsettia selection, not patented.

*Male parent.*—Unidentified proprietary Poinsettia selection, not patented.

Propagation:

*Type cutting.*—Terminal cuttings.

*Time to initiate roots.*—Summer: About 14 to 18 days at 20 to 22° C. Winter: About 15 to 19 days at 24° C.

*Time to develop roots.*—Summer: About 24 days at 20° C. Winter: About 24 days at 22° C.

*Rooting habit.*—Thick, freely branching.

Plant description:

*Plant form.*—Inverted triangle, top of plant rounded; mounding.

*Growth habit.*—Compact, upright and spreading. Very freely branching. Branching is enhanced by removing the shoot apex. Moderate vigor to vigorous.

*Plant height.*—About 27 cm.

*Crop time.*—From unrooted cuttings to a flowering plant in a 16.5-cm container, about 17 weeks are required.

*Stem description.*—Number of lateral branches: About 9 lateral branches develop after removal of the terminal apex. Lateral branch length: About 18 cm. Internode length: About 7.5 mm. Stem color: 144A.

*Foliage description.*—Quantity of leaves per lateral branch: About 10. Length: About 11 cm. Width: About 6.5 cm. Shape: Mostly ovate. Apex: Acuminate. Base: Rounded acute. Margin: Entire. Texture: Smooth. Mostly glabrous with very slight pubescence on lower surface. Color: Young foliage, upper surface: 147A. Young foliage, lower surface: 147B. Mature foliage, upper surface: Darker than 147A . Mature foliage, lower surface: 137C. Venation, upper surface: 146C. Venation, lower surface: 147C. Petiole: Length: About 3.5 cm. Diameter: About 2 mm. Color: 146C.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Early flowering, response time is about 8.5 weeks.

*Quantity of inflorescences.*—One per lateral branch, usually about 9 per plant.

*Inflorescence size.*—Diameter: About 29 cm. Height (depth): About 3 cm.

*Flower bracts.*—Quantity of flower bracts per inflorescence: Usually about 14 primary bracts and about 6 smaller secondary bracts per inflorescence. Length, largest bracts: About 12 cm. Width, largest bracts: About 7 cm. Shape: Mostly ovate. Apex: Acuminate. Base: Acute. Margin: Entire. Texture: Smooth. Aspect: Mostly flat, occasionally slightly rugose. Color: Developing, upper surface: 51C with random flecks of 51A and 51B. Developing, lower surface: 50D with random flecks of 50B and 50C. Mature, upper surface: 38B with random flecks of 50B; fading to 29C to 29D with random flecks of 51B with subsequent development. Mature, lower surface: 38A to 38B.

*Cyathia.*—Quantity: Usually about 14 per corymb. Diameter of cyathia cluster: About 3.5 by 4.5 cm. Length: About 1.1 cm. Width: About 7 mm. Color: Immature: 144A. Mature: 144B. Peduncle: Length: About 4 mm. Aspect: Strong, erect. Color: 144B. Stamens: Stamen number: Typically more than 20 per cyathium. Anther shape: Oblong. Anther length: About 1 mm. Anther color: 13C. Amount of pollen: Moderate. Pollen color: 13A. Pistils: Not commonly observed. Length: About 7 mm. Stigma color: 60B. Style color: 144C. Nectary color: 13A.

Disease resistance: Resistance to pathogens common to Poinsettias has not been observed on plants grown under commercial conditions.

Post-production longevity: Generally plants maintain good substance and bract color for about six weeks under interior conditions.

It is claimed:

1. A new and distinct cultivar of Poinsettia plant named 'Amazone', as illustrated and described.

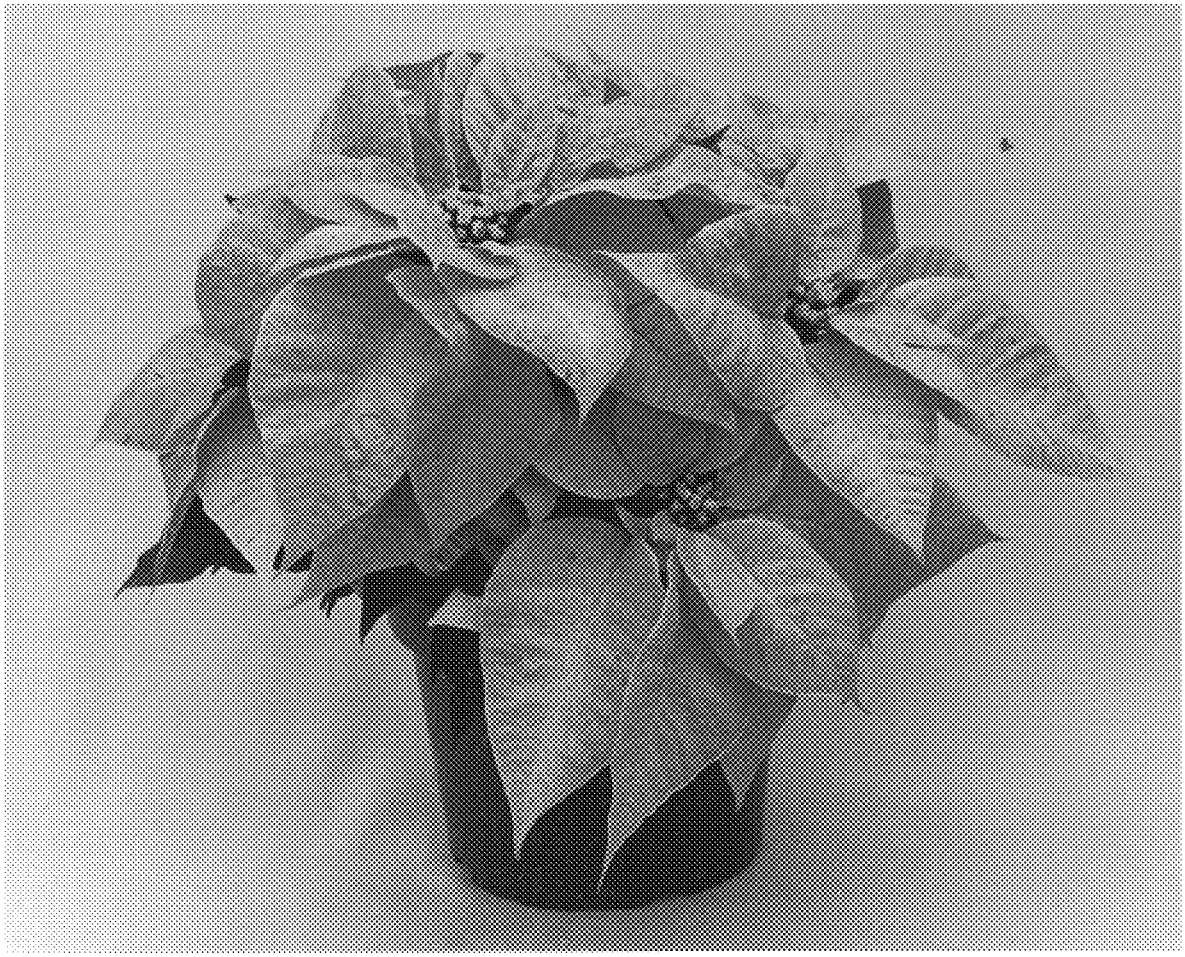
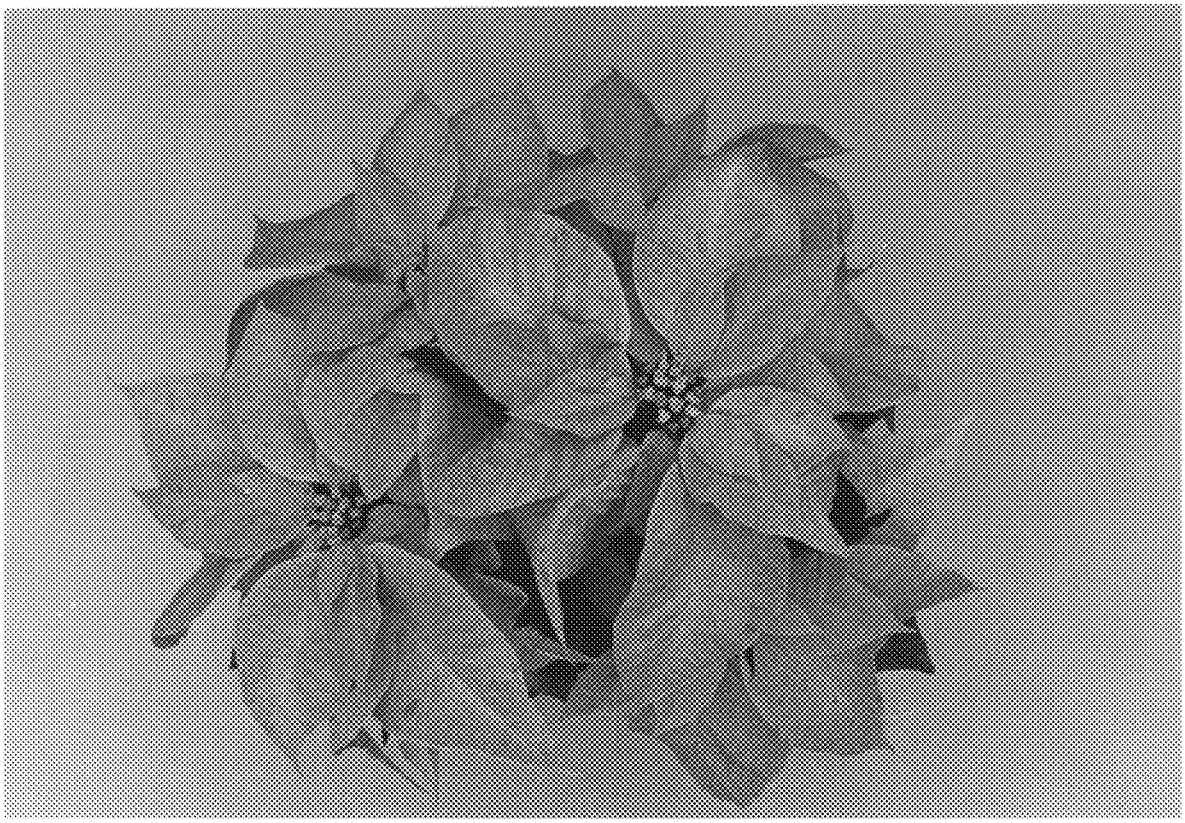

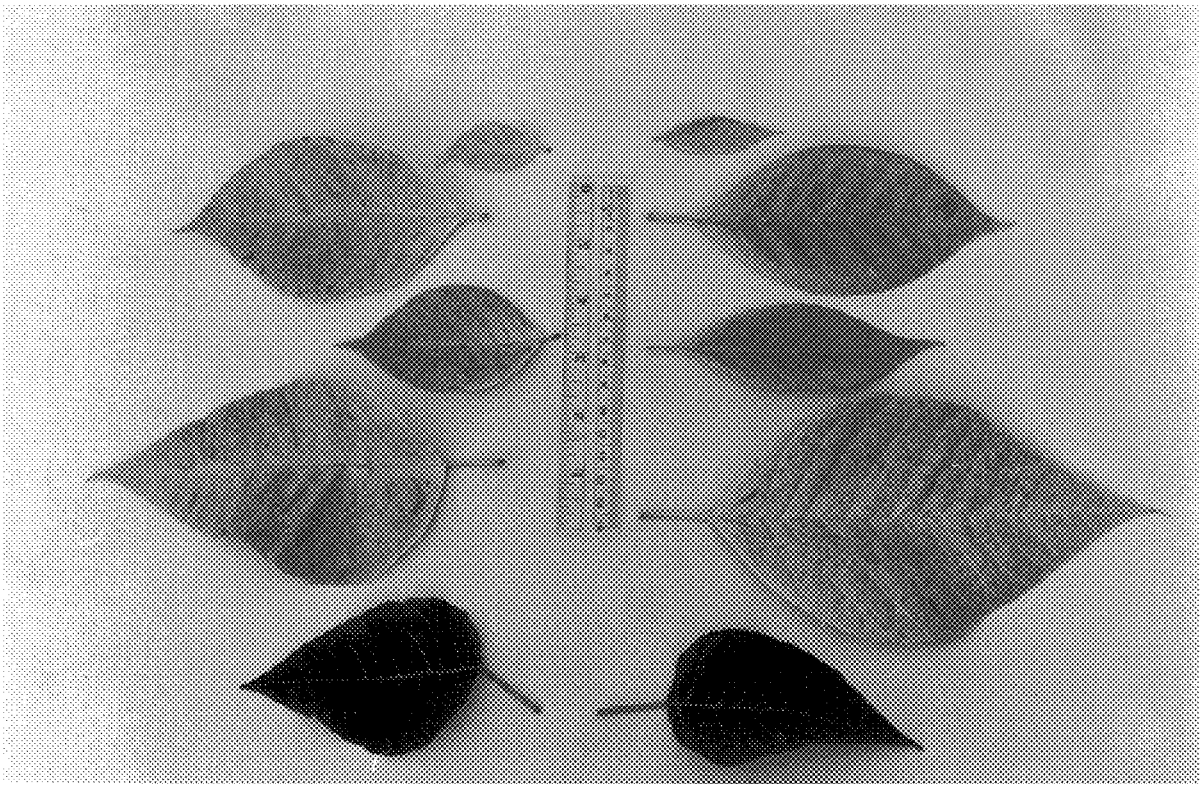

* * * * *